US00PP34991P2

(12) United States Plant Patent
Nelson et al.

(10) Patent No.: US PP34,991 P2
(45) Date of Patent: Feb. 21, 2023

(54) STRAWBERRY PLANT NAMED 'FPS-14_540-041'

(50) Latin Name: ***Fragaria* x *ananassa***
Varietal Denomination: FPS-14_540-041

(71) Applicant: Fragaria Plant Sciences, B.V., Veldoven (NL)

(72) Inventors: Jonathan R. Nelson, Watsonville, CA (US); Daniel S. Nelson, Watsonville, CA (US); Scott C. Nelson, Watsonville, CA (US); Jeffrey D. Nelson, Watsonville, CA (US)

(73) Assignee: FRAGARIA PLANT SCIENCES, B.V., Veldoven (NL)

( * ) Notice: Subject to any disclaimer, the term of this patent is extended or adjusted under 35 U.S.C. 154(b) by 0 days.

(21) Appl. No.: 17/886,402

(22) Filed: Aug. 11, 2022

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP26,193 P3 12/2015 Ackerman et al.

*Primary Examiner* — Susan McCormick Ewoldt
(74) *Attorney, Agent, or Firm* — Foley & Lardner LLP

(57) ABSTRACT

This invention relates to a new and distinct variety of strawberry plant named 'FPS-14_540-041'. This new strawberry plant named 'FPS-14_540-041' is primarily adapted to the growing conditions of the central coast of California, and is primarily characterized by its red fruit color, medium fruit size, and long conical fruit shape; good fruit flavor, good skin firmness, with seeds typically held even with to slightly above the surface; very smooth fruit surface, even in color, with a slight difference in size between primary and secondary fruit; unique trait of a large first flush, followed by an even larger second flush of fruit in the late season; medium plant size, upright in habit with and medium density; medium to dark green foliage color, and medium foliage size; and fruiting trusses typically held above to level with the plant, with low to medium pubescence.

5 Drawing Sheets

Latin name of the genus and species of the plant claimed: *Fragaria* x *ananassa.*

Variety denomination: 'FPS-14_540-041'.

BACKGROUND OF THE INVENTION

The present invention relates to a new and distinct strawberry variety named 'FPS-14_540-041'. This new variety is a result of a controlled cross made in 2014 in an ongoing breeding program between strawberry variety designated 'Malling Centenary' as the seed (female) parent, and strawberry variety designated 'PE-3.211' (U.S. Plant Pat. No. 26,193) as the pollen (male) parent. The variety is botanically known as *Fragaria* x *ananassa.*

The seedling resulting from the aforementioned cross was selected from a controlled breeding plot in Santa Cruz County, Calif. in the Spring of 2016. After its selection, the new variety was asexually propagated by stolons in San Joaquin County, Calif. The new variety was tested extensively over the next several years in fruiting fields in Santa Cruz County, Calif. This propagation has demonstrated that the combination of traits disclosed herein as characterizing the new variety are fixed and remain true-to-type through successive generations of asexual reproduction.

BRIEF SUMMARY OF THE INVENTION

'FPS-14_540-041' is primarily adapted to the climate and growing conditions of the central coast of California. The nearby Pacific Ocean provides the humidity and moderate temperatures needed to produce a strong, vigorous plant and maintain fruit quality during the spring through summer production months.

The following traits have been repeatedly observed and are determined to be unique characteristics of 'FPS-14_540-041', which in combination distinguish this strawberry plant as a new and distinct variety:

1. Fruit is red in color, medium in size, and long conical in shape;
2. Fruit has good flavor, good skin firmness, with seeds typically held even with to slightly above the surface;
3. Fruit surface is very smooth, even in color, with a slight difference between primary and secondary fruit;
4. Plant has a unique trait of a large first flush, then follows up with an even larger second flush of fruit in the late season;
5. Plant is medium in size, upright in habit with medium density; and
6. Fruiting trusses are typically held above to level with the plant, with low to medium pubescence.

The strawberry variety that is believed to be most closely related to the new variety 'FPS-14_540-041' is 'PE-3.211' (U.S. Plant Pat. No. 26,193). In side-by-side comparisons to the similar strawberry variety 'PE-3.211', 'FPS-14_540-041' differs by the following combination of characteristics as described in Table 1.

TABLE 1

| Characteristic | 'FPS-14_540-041' | 'PE-3.211' (U.S. Plant Pat. No. 26,193) |
|---|---|---|
| Fruit: color | Red | Orange red |
| Fruit: season average size (grams) | 24.1 | 19.9 |
| Terminal leaflet: shape of base | Obtuse | Acute |
| Terminal leaflet: margins (shape of teeth) | Acute | Obtuse |
| Seeds: insertion of achenes | Level to above surface | Level with surface |
| Petiole: Size (cm) | 18.2 cm | 13.3 cm |
| Petiole: attitude of hairs (pubescence) | Slight to strongly outward | Slightly outward |
| Stipule: anthocyanin intensity | Medium to strong | Absent or weak |
| Fruiting truss: position relative to foliage | Level with to above | Beneath to level with |

For identification, a series of molecular markers have been determined for this new variety.

'FPS-14_540-041' differs from its parents, 'Malling Centenary' and 'PE-3.211' (U.S. Plant Pat. No. 26,193) by the following combination of characteristics as described in Tables 2 and 3.

TABLE 2

| Characteristic | 'FPS-14_540-041' | 'Mailing Centenary' |
|---|---|---|
| Fruit: color | Red to dark red | Orange red |
| Fruit: shape | Conical to rhomboid | Conical |
| Fruit: flavor | Fair | Good |
| Plant: type | June bearer with summer long production | June bearer |

TABLE 3

| Characteristic | 'FPS-14_540-041' | 'PE-3.211' (U.S. Plant Pat. No. 26,193) |
|---|---|---|
| Plant: type | June bearer | Everbearer (remontant) |
| Fruit: firmness of flesh | Medium | Firm |
| Fruit: flavor | Average | Very good |
| Plant: size | Medium | Medium to large |

BRIEF DESCRIPTIONS OF THE PHOTOGRAPHS

The accompanying color photographs illustrate the overall appearance of typical specimens of the new strawberry variety 'FPS-14_540-041' at various stages of development, as true as it is reasonably possible with color reproductions of this type. Color in the photographs may differ slightly from the color value cited in the botanical descriptions which accurately describe the color of 'FPS-14_540-041'. The depicted plant and plant parts of the new strawberry variety 'FPS-14_540-041' are approximately three to four months old. The photographs were taken in Santa Cruz County, Calif.

DETAILED BOTANICAL DESCRIPTION

Figure 1:
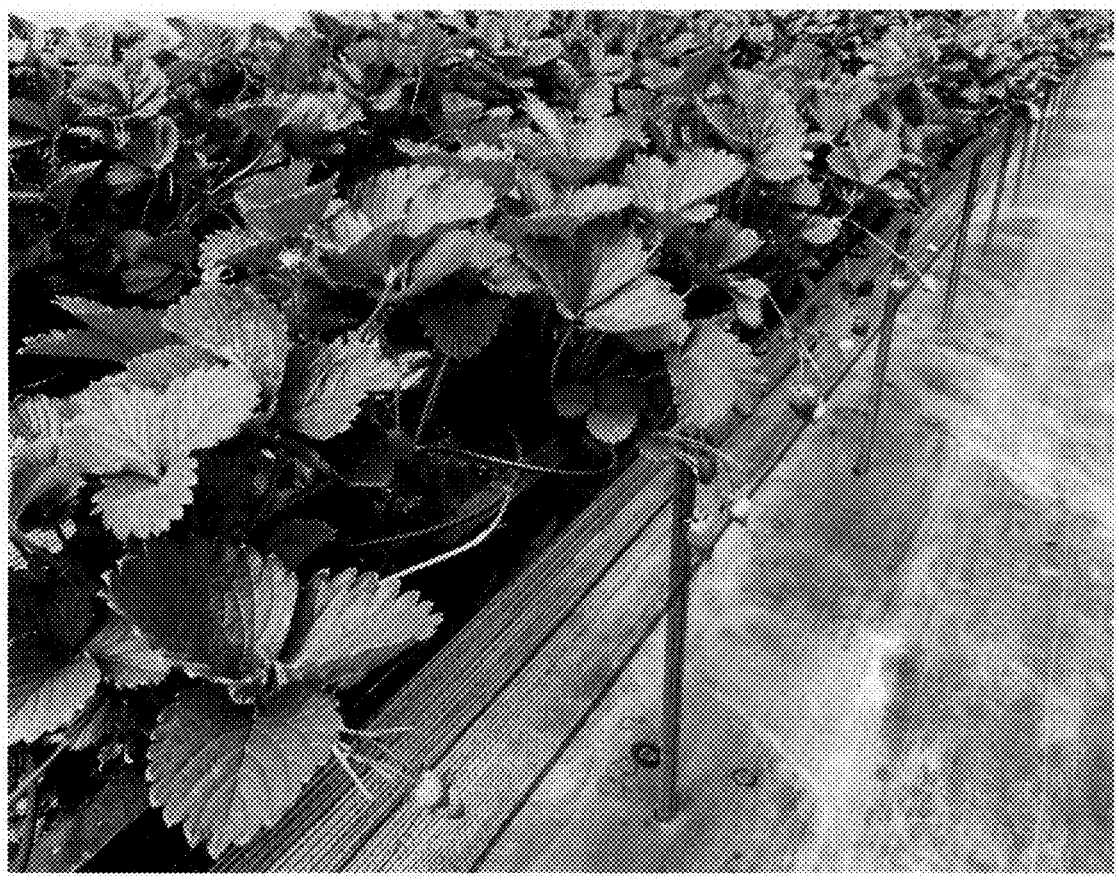
FIG. 1 shows fruiting field characteristics of 'FPS-14_540-041', taken in the month of June 2022.
Figure 2:
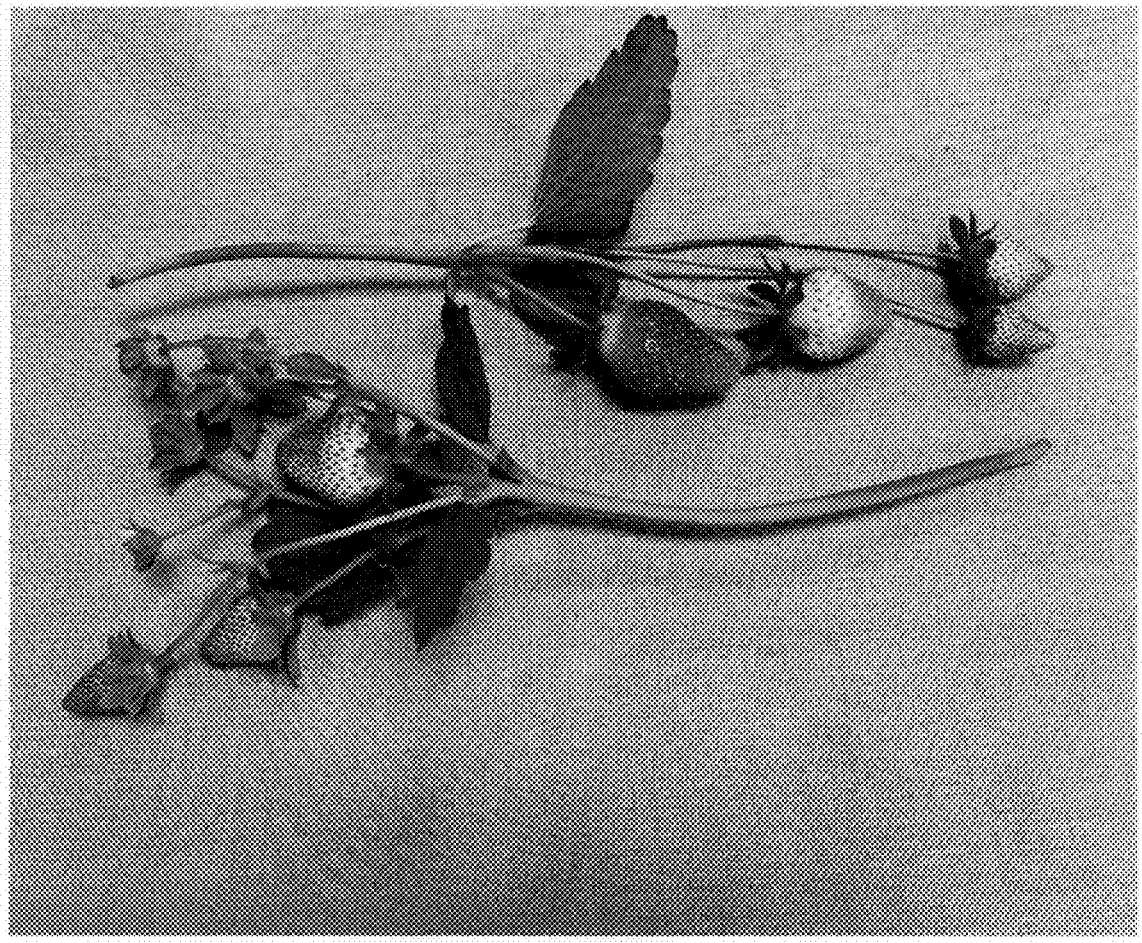
FIG. 2 shows typical fruiting truss and truss parts of 'FPS-14_540-041', taken in the month of June 2022.
Figure 3:
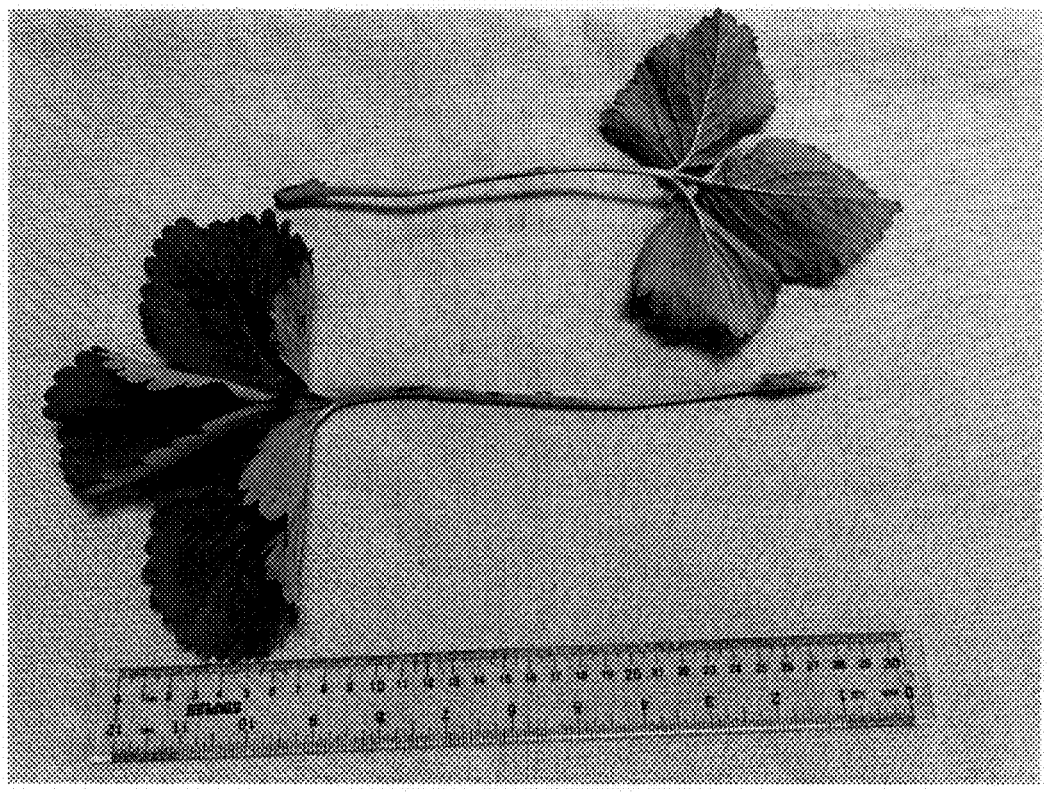
FIG. 3 shows upper and lower surfaces of leaf and leaf parts of 'FPS-14_540-041', taken in the month of June 2022.
Figure 4:
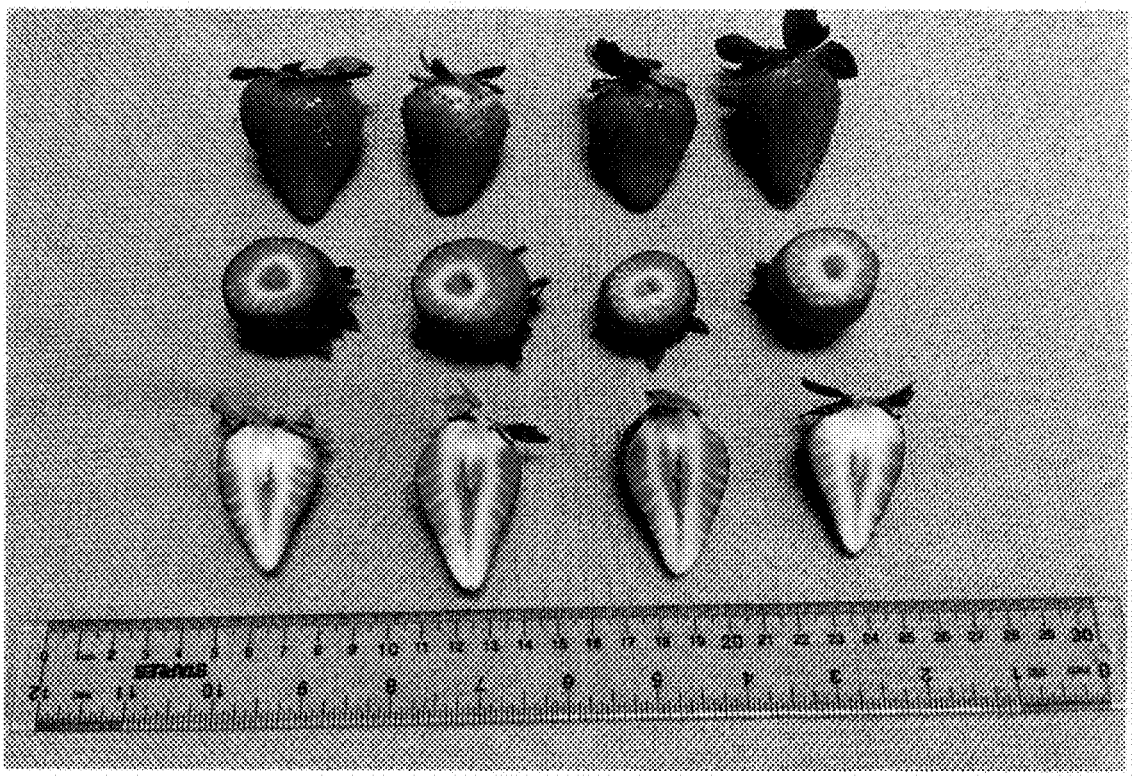
FIG. 4 shows internal and external mature fruit characteristics of 'FPS-14_540-041', taken in the month of June 2022.
Figure 5:
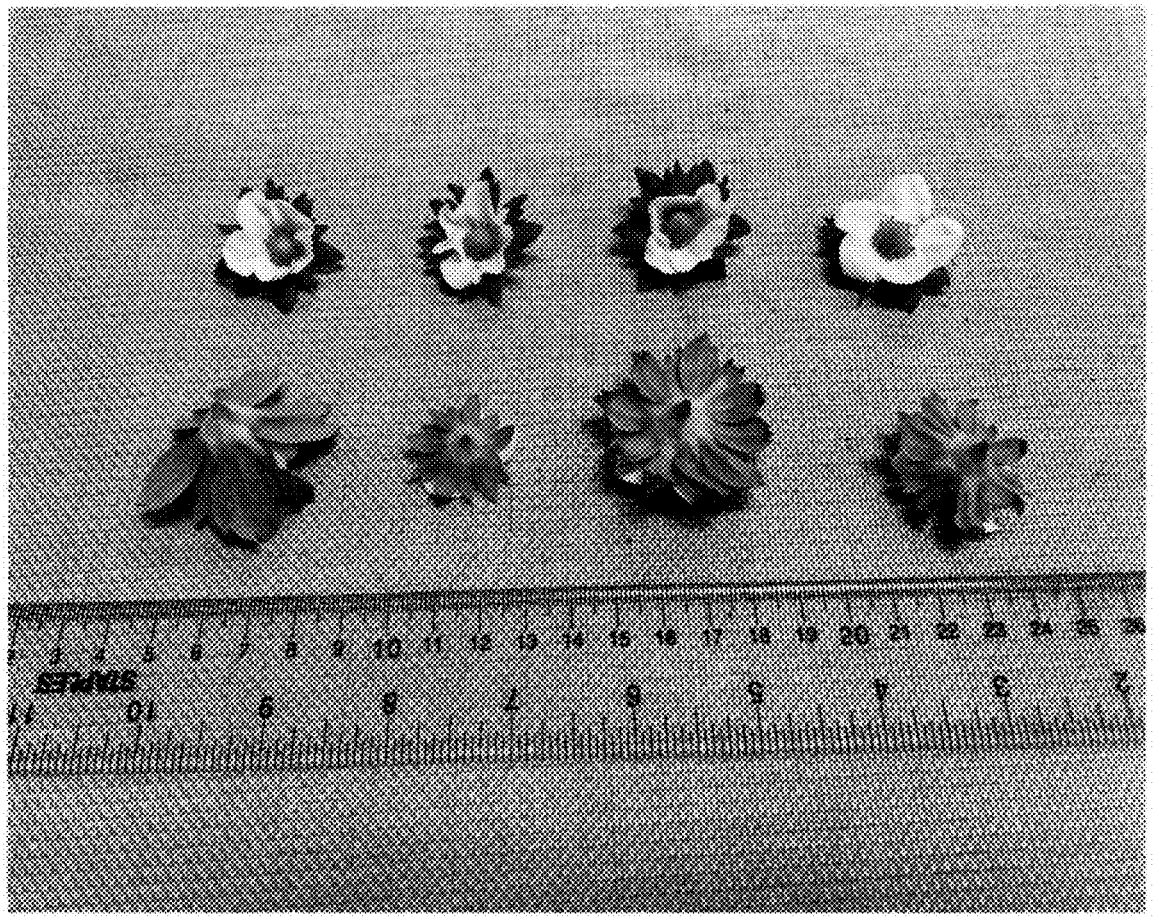
FIG. 5 shows upper and lower surfaces of flower and flower parts of 'FPS-14_540-041', taken in the month of June 2022.

The new variety 'FPS-14_540-041' has not been observed under all possible environmental conditions. The characteristics of the new variety 'FPS-14_540-041' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'FPS-14_540-041', unless otherwise noted, are based on observations taken during the 2022 growing season in Santa Cruz County, Calif. These measurements and ratings were taken from plants of 'FPS-14_540-041' dug from a low-elevation nursery located in San Joaquin County, Calif. in December 2021 and planted approximately two months later in Santa Cruz County, Calif. The approximate age of the observed plants is three to four months. Yield observations including average weight and marketable yield, along with fruit quality characteristics including soluble solids, are averaged from five years of data collected from the 2018 through 2022 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London, Sixth Edition (2015).

The following characteristics describe fruit, plant, stolon, foliage, fruiting truss, flower, reproductive organs and pest and disease characteristics of the new strawberry 'FPS-14_540-041'.

Fruit characteristics:

*Color of mature fruit*.—RHS 45B (red).
*Color of internal flesh*.—RHS 43A (medium red).
*Color of core*.—RHS 42B (light red).
*Average length (cm)*.—5.1.
*Average width (cm)*.—3.5.
*Size*.—Ranges from medium to large.
*Average length/width ratio*.—1.44 (slightly longer than broad).
*Hollow center average length (mm)*.—3.0.
*Hollow center average width (mm)*.—1.0.
*Hollow center expression*.—Weak.
*Season average weight (gm)*.—24.7.
*Marketable yield season (gm/plant)*.—394.
*Predominant shape*.—Ranges from conical to rhomboid.
*Difference in shape between primary and secondary fruit*.—None or very slight.
*Band without achenes*.—Medium.
*Evenness of surface*.—Even or very slightly uneven.
*Evenness of color*.—Even or very slightly uneven.

*Glossiness*.—Strong.
*Insertion of achenes*.—Ranges from level with surface to above surface.
*Average calyx diameter* (*cm*).—3.9.
*Position of calyx attachment*.—Ranges from level to raised.
*Attitude of sepals*.—Outward.
*Size of calyx in relation to fruit diameter*.—Slightly larger.
*Adherence of calyx* (*when fully ripe*).—Strong.
*Firmness of flesh*.—Medium.
*Keeping quality*.—Good.
*Fruit market*.—Fresh.
*Post-harvest fruit longevity* (*at* 1 *to* 3 *degrees Celsius*) .—Moderate to fair (5 to 7 days).
*Distribution of red color of the flesh*.—Marginal and central.
*Flavor*.—Good.
*Soluble solids* (% *brix*).—7.9.
*Achene color, shaded side*.—RHS 151C (yellow green group).
*Achene color, sun-exposed side*.—RHS 183D (greyed purple group).
*Achene average length* (*mm*).—1.6.
*Achene average width* (*mm*).—1.1.
*Achene average weight* (*mg*).—0.5.
*Achene average quantity per berry*.—230.
*Achene shape*.—Ovate.

Time of flowering:
*Flowering season* (50% *of plants with at least one flower*).—Ranges from medium to late (May through July in Santa Cruz County, Calif.).
*Maturing season* (50% *of plants with mature fruit*.—Ranges from medium to late (May through July in Santa Cruz County, Calif.).
*Flowering season*.—April through July (in Santa Cruz County, Calif.).
*Harvest season*.—May through July (in Santa Cruz County, Calif.).
*Harvest maturity*.—Mid to late season (May through July).
*Plant hardiness*.—Zone 9 (USDA Plant Hardiness Zone Map).
*Type of bearing*.—Partially remontant (summer bearer).

Plant characteristics:
*Average height* (*cm*).—26.3.
*Average spread* (*cm*).—31.5.
*Average crowns per plant*.—3.3.
*Size*.—Medium.
*Habit*.—Upright.
*Density*.—Medium.
*Vigor*.—Medium.

Stolon characteristics:
*Color*.—RHS 144B (yellow green group).
*Anthocyanin coloration*.—RHS 184B (greyed purple group).
*Anthocyanin intensity*.—Very strong.
*Pubescence*.—Medium.
*Attitude of hairs*.—Upward.
*Average quantity in nursery* (*per square foot*).—4 to 5 (medium).
*Average diameter at first bract* (*mm*).—4.0 (medium).
*Length from mother plant to first daughter* (*cm*).—30.3.

Terminal leaflet characteristics:
*Average length* (*cm*).—9.0.
*Average width* (*cm*).—7.9.
*Average area terminal* ($cm^2$).—71.4.
*Average length/width ratio*.—1.14 (longer than broad).
*Shape of base*.—Obtuse.
*Shape of apex*.—Obtuse.
*Margins* (*shape of teeth*).—Acute (serrate).
*Average serrations per leaf*.—22.5.

Foliage characteristics:
*Color of upper surface*.—RHS 139B (medium yellow green).
*Color of lower surface*.—RHS 147C (yellow green group).
*Color of venation, upper surface*.—RHS 151B (yellow green group).
*Color of venation, lower surface*.—RHS 145A (yellow green group).
*Number of leaflets*.—3.
*Leaf size*.—Ranges from medium to small.
*Average length* (*cm*).—9.1.
*Average width* (*cm*).—17.8.
*Average area foliage* ($cm^2$).—162.1.
*Shape in cross section*.—Strongly to slightly concave.
*Interveinal blistering*.—Medium.
*Texture of upper surface*.—Medium.
*Texture of lower surface*.—Smooth.
*Venation pattern*.—Pinnate reticulate.
*Leaf glossiness*.—Absent or weak.
*Leaf variegation*.—Absent.

Petiole characteristics:
*Petiole color*.—RHS N144C (yellow green group).
*Petiole average length* (*cm*).—18.2.
*Petiole average diameter* (*mm*).—4.2.
*Attitude of hairs*.—Ranges from slightly outward to strongly outward.
*Frequency of bract leaflets*.—1% to 2% (ranges from few to none).
*Size of bract leaflets*.—Small.
*Pubescence*.—Moderate.
*Petiolule color*.—RHS N144C (yellow green group).
*Petiolule average length* (*mm*).—9.0.
*Petiolule average diameter* (*mm*).—2.4.

Stipule characteristics:
*Color*.—RHS N144C (yellow green group).
*Anthocyanin coloration*.—RHS 60C (red purple group).
*Anthocyanin intensity*.—Ranges from medium to strong.
*Average length* (*mm*).—28.5.
*Average width* (*mm*).—9.8.
*Shape*.—Triangular.
*Texture*.—Light.
*Shape of base*.—N/A.
*Shape of apex*.—Acute.
*Margins*.—Entire (smooth).

Fruiting truss characteristics:
*Anthocyanin coloration*.—RHS 182B (greyed red group).
*Anthocyanin intensity*.—Absent or very weak.
*Average length at maturity* (*cm*).—19.8.
*Position relative to foliage*.—Ranges from level with to above.
*Flower quantity* (*season average per plant*).—59.8 (ranges from medium to many).

*Average fruit quantity per truss.*—5.3 (medium).
*Attitude at first pick.*—Ranges from prostrate to semi-erect.
*Primary pedicel color.*—RHS 144A (yellow green group).
*Primary pedicel average length (cm).*—5.0.
*Primary pedicel average diameter (mm).*—3.5.
*Pedicel attitude of hairs.*—Ranges from upward to slightly outward.
*Pedicel texture.*—Ranges from medium to strong.
*Primary peduncle color.*—RHS 144A (yellow green group).
*Primary peduncle average length (cm).*—14.2.
*Primary peduncle average diameter (mm).*—5.9.
*Peduncle texture.*—Medium.

Flower characteristics:
*Petal color, upper surface.*—RHS 155C (white group).
*Petal color, lower surface.*—RHS 155C (white group).
*Petal average length (mm).*—10.3.
*Petal average width (mm).*—11.3.
*Petal average length/width ratio.*—0.92 (broader than long).
*Average petal quantity per flower.*—5.
*Petal shape.*—Rounded.
*Petal texture, upper surface.*—Smooth.
*Petal texture, lower surface.*—Smooth.
*Petal shape of base.*—Acute.
*Petal shape of apex.*—Rotund.
*Petal margins.*—Entire (smooth).
*Sepal color, upper surface.*—RHS 144A (yellow green group).
*Sepal color, lower surface.*—RHS 144B (yellow green group).
*Sepal average length (mm).*—14.2.
*Sepal average width (mm).*—6.3.
*Sepal average length/width ratio.*—2.26.
*Average sepal quantity per flower.*—11.5.
*Sepal shape.*—Elliptical.
*Sepal texture, upper surface.*—Ranges from smooth to light.
*Sepal texture, lower surface.*—Smooth.
*Sepal shape of apex.*—Acute.
*Sepal margins.*—Entire (smooth).
*Flower bud color.*—RHS 145A (yellow green group).
*Flower bud shape.*—Bell.
*Flower bud average length (mm).*—14.3.
*Flower bud average diameter (mm).*—7.2.
*Corolla average diameter (mm).*—23.7 (medium).
*Flower average depth (mm).*—10.0 (medium).
*Calyx average diameter (mm).*—38.5.
*Size of calyx relative to corolla.*—Larger.
*Relative position of petals (flowers with 5 or 6 petals).*—Overlapping.
*Size of inner calyx relative to outer calyx.*—Smaller.

Reproductive organs:
*Anther color.*—RHS 13A (yellow group).
*Filament color.*—RHS 145C (yellow green group).
*Filament average length (mm).*—2.7.
*Anther average length (mm).*—1.6.
*Anther average width (mm).*—1.0.
*Anther shape.*—Broad elliptic.
*Pollen amount.*—Abundant.
*Ovary color.*—RHS 147C (yellow green group).
*Style color.*—RHS 151C (yellow green group).
*Pistil average quantity per flower.*—300.
*Pistil average length (mm).*—1.0.
*Style average length (mm).*—1.1.
*Stigma average diameter (mm).*—0.2.
*Stigma shape.*—Rounded.

Disease and pest reactions:
*Powdery mildew (Sphaerotheca macularis).*—Ranges from moderate to moderately susceptible.
*Angular leaf spot (Xanthomonas fragariae).*—Moderately susceptible.
*Botrytis fruit rot (Botrytis cinerea).*—Moderately susceptible.
*Fusarium wilt (Fusarium oxysporum).*—Resistant.
*Anthracnose crown rot (Colletotrichum fragariae).*—Unknown.
*Two-spotted spider mite (Tetranychus urticae).*—Unknown.

We claim:

1. A new and distinct strawberry plant named 'FPS-14_540-041', as herein described and illustrated by the characteristics set forth above.

* * * * *